(12) United States Patent
Jolles et al.

(10) Patent No.: US 7,687,060 B2
(45) Date of Patent: Mar. 30, 2010

(54) METHOD FOR THE TREATMENT OR PROPHYLAXIS OF TUBERCULOSIS

(75) Inventors: Stephen Jolles, Mill Hill (GB); Ricardo Tascon, Mill Hill (GB); Douglas Lowrie, Mill Hill (GB); Vangelis Stavropoulos, Mill Hill (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 11/371,262

(22) Filed: Mar. 8, 2006

(65) Prior Publication Data

US 2006/0275311 A1 Dec. 7, 2006

Related U.S. Application Data

(63) Continuation of application No. PCT/GB2004/003830, filed on Sep. 8, 2004.

(30) Foreign Application Priority Data

| Sep. 8, 2003 | (GB) | ................................ | 0320987.1 |
| Sep. 23, 2003 | (GB) | ................................ | 0322288.2 |
| Feb. 3, 2004 | (GB) | ................................ | 0402358.6 |

(51) Int. Cl.
*A61K 39/395* (2006.01)
*A61K 39/40* (2006.01)
*C07K 16/00* (2006.01)

(52) U.S. Cl. .............. 424/130.1; 424/131.1; 424/164.1; 424/168.1; 530/387.1; 530/389.2; 530/389.5

(58) Field of Classification Search ........................ None
See application file for complete search history.

(56) References Cited

U.S. PATENT DOCUMENTS 6,531,464 B1 * 3/2003 Szabo et al. ................. 514/183

FOREIGN PATENT DOCUMENTS

WO  WO 02/096455 A2 * 12/2002

OTHER PUBLICATIONS

Hemming et al.Clin. Diagn Lab. Immunol. Sep. 2001, p. 859-863.*
Sabchareon et al. Am J Trop med Hyg Sep. 1991 45(3):297-308.*
Taylor et al. Clin Exp Immunol Dec. 1992 90(3):357-62.*
Rowena et al. Pediatric Dermatology 2000 vol. 17 No. 3, 208-212.*
Jolles et al. Conference proceeding of the International symposium on Intravenous Immunoglobulin Therapy, 5th, Interlaken Switzerland, Sep. 25-27, 2003 published in Intravenous Immunoglobulin in the Third Millennium, edited by Dalakas et al.2004 p. 337-339.*
Roy et al. Infection and Immunity, Sep. 2005, p. 6101-6109.*
Undar et al. Acta Haematologica (Basel), 1996 vol. 96:73-78.*
Sandoglobulin® technical bulletin, Novartis, 2000.*
Rowena et al. Pediatric Dermatology vol. 17 No. 3 p. 208-212, 2000.*
Hemming et al. Clinical and Diagnostic Laboratory Immunology Sep. 2001 p. 859-863.*
(Abbas et al. Cellular and Molecular Immunology 4th edition, 2000, p. 362.*
Definition of Prophylaxis: Stedmans Medical Dictionary.*
Pyne et al. Rheumatology 2002; 41:367-374.*
Jordan et al. Transplantation Sep. 27, 1998; 66(6):800-5.*
Turczynowski, Roman. Polish Medical Science and History Bulletin Jan; 13(1):40-2, 1970.*
Glatman-Freedman et al (FEMS Immunology and Medical Microbiology 39 (2003) 9-16).*

* cited by examiner

*Primary Examiner*—Robert B. Mondesi
*Assistant Examiner*—Oluwatosin Ogunbiyi
(74) *Attorney, Agent, or Firm*—Edwards Angell Palmer & Dodge LLP; Kathleen Williams; Elbert Chiang

(57) ABSTRACT

The invention provides the use of intravenous immunoglobulin (IVIg) in the preparation of a medicament for the treatment and/or prophylaxis of mycobacterial infection.

18 Claims, 9 Drawing Sheets

Lung Control x40 Day 42

Lung IVIg x40 Day 42

Lung Control x100 Day 42

Lung IVIg x100 Day 42

METHOD FOR THE TREATMENT OR PROPHYLAXIS OF TUBERCULOSIS

RELATED APPLICATIONS

Figure 1:
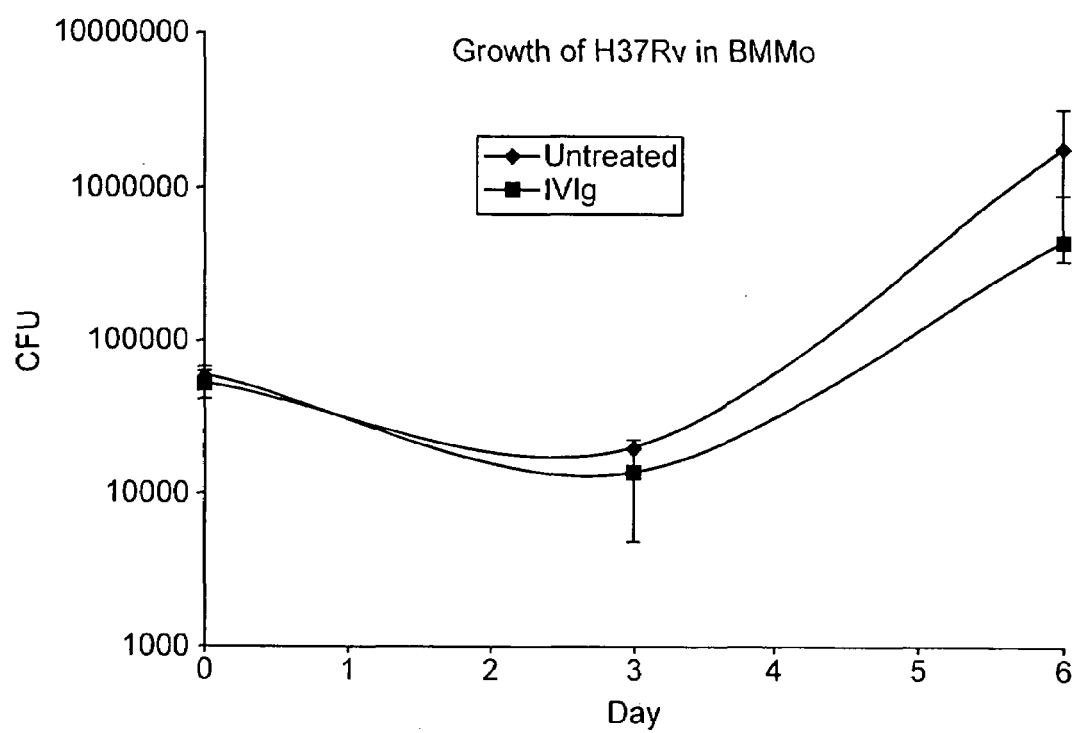
Figure 2:
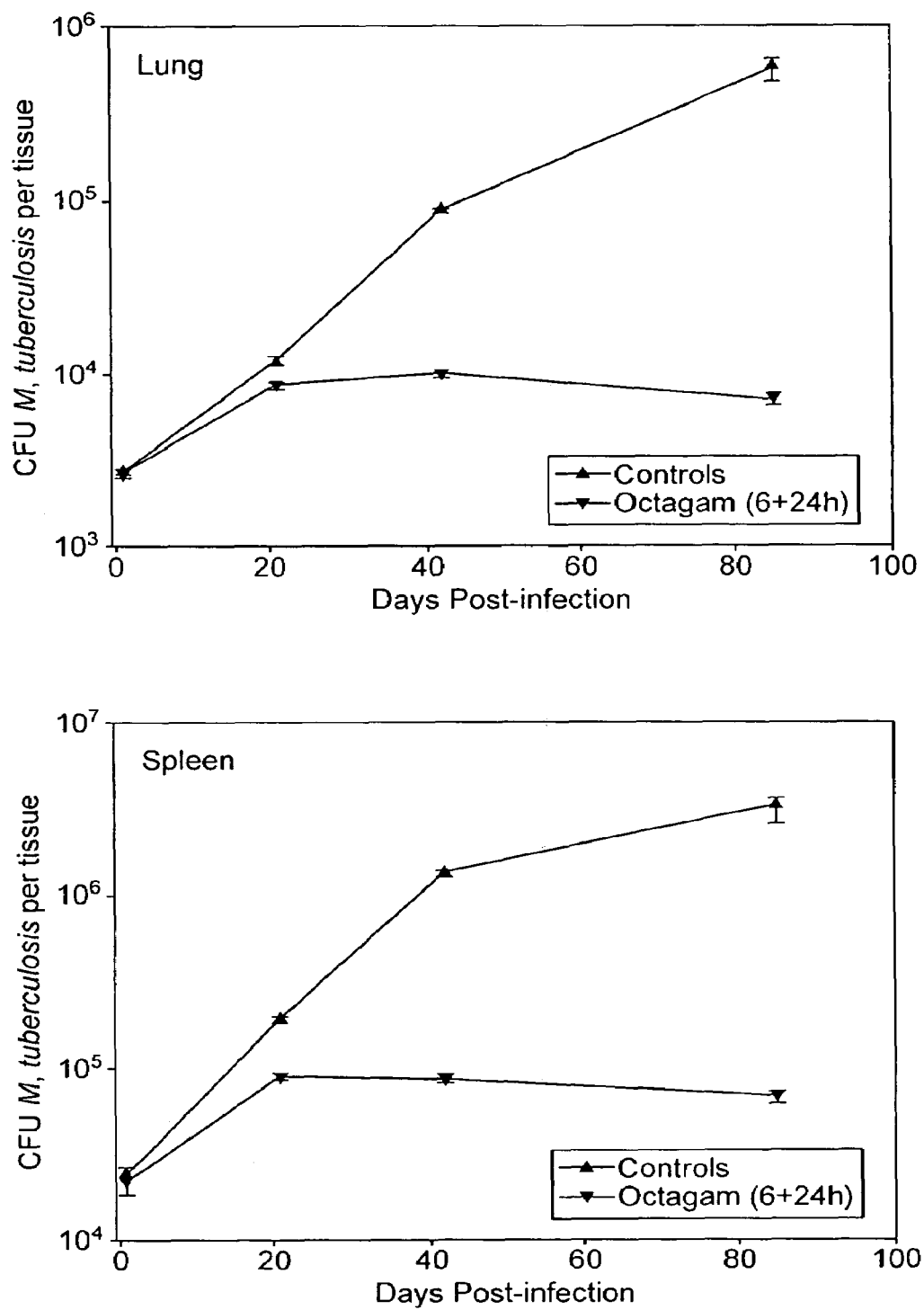
Figure 2:
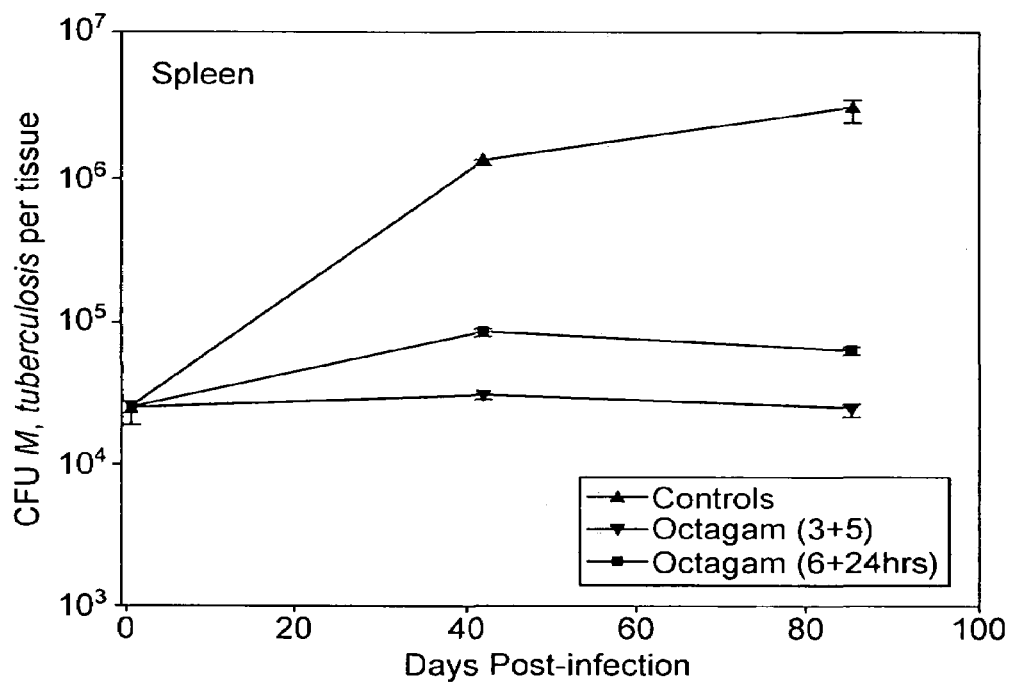
Figure 2:
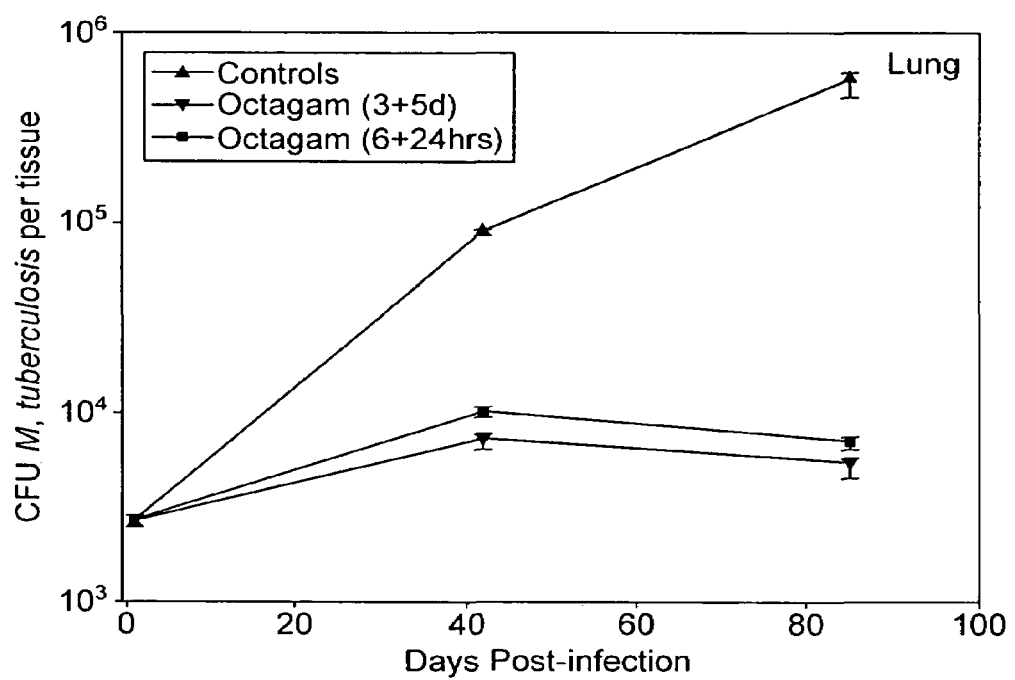
Figure 3:
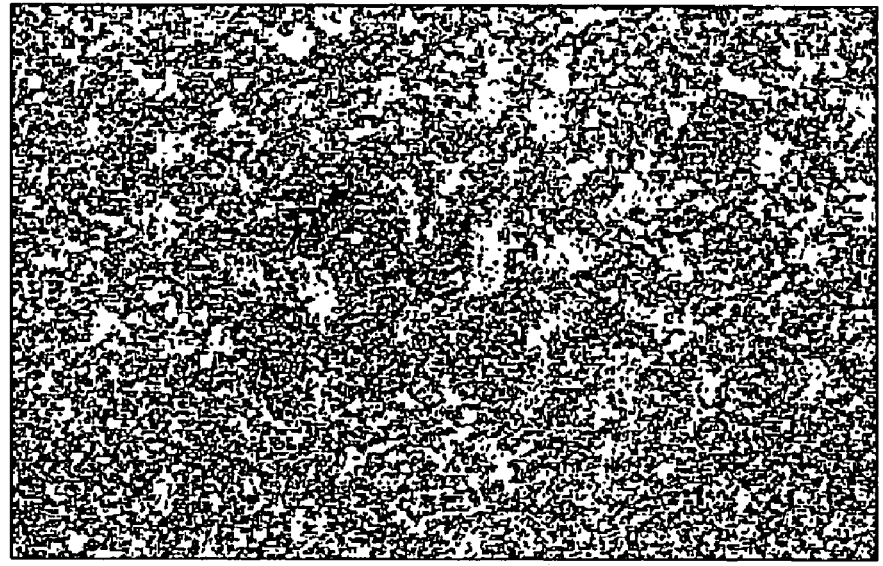
Figure 3:
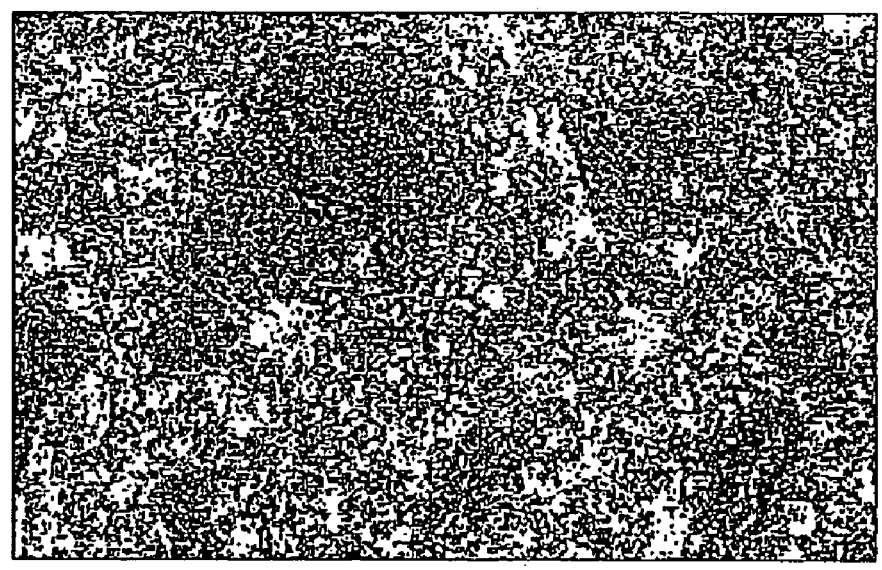
Figure 3:
Figure 3:
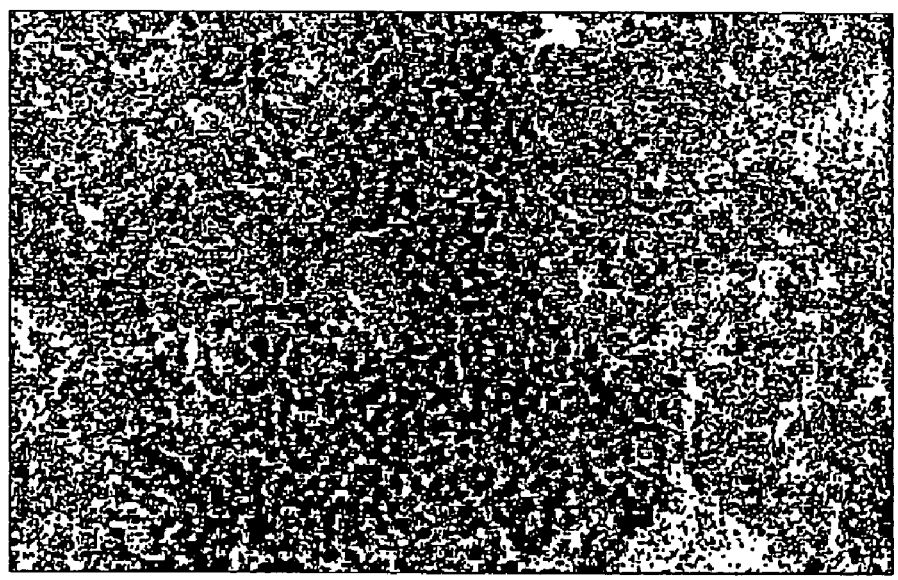
Figure 4:
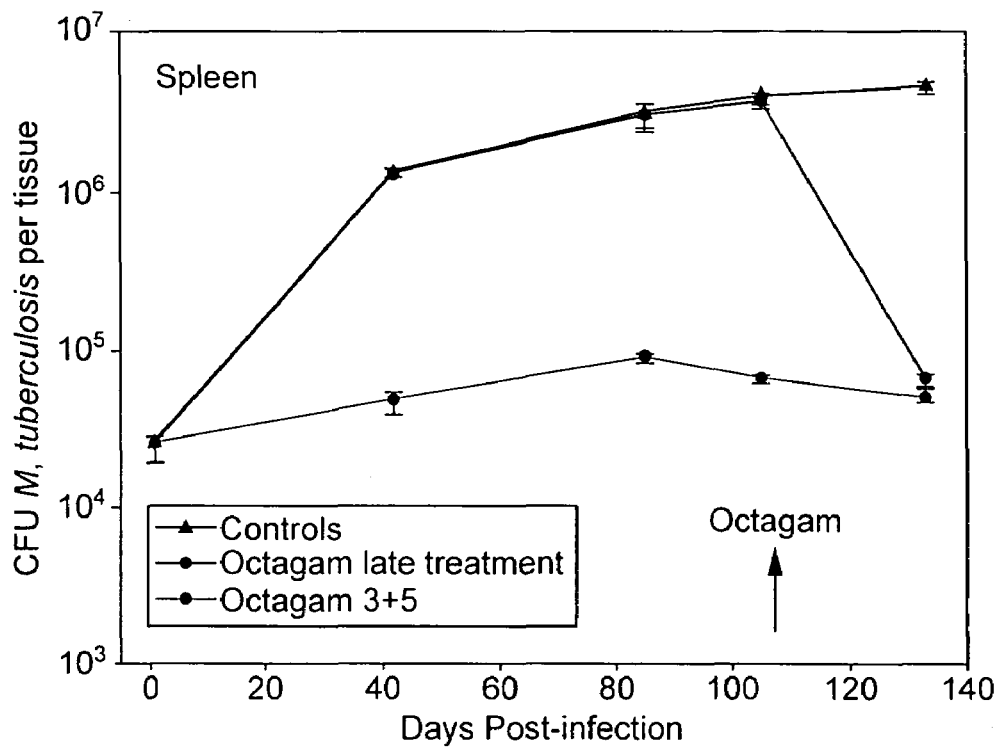
Figure 4:
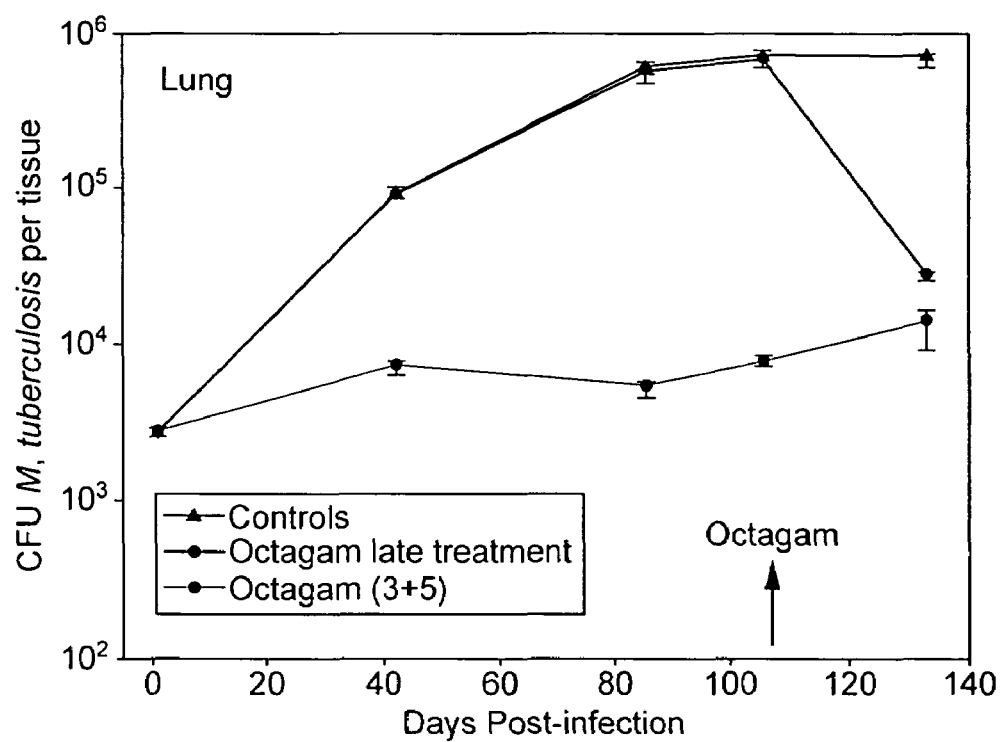
Figure 5:
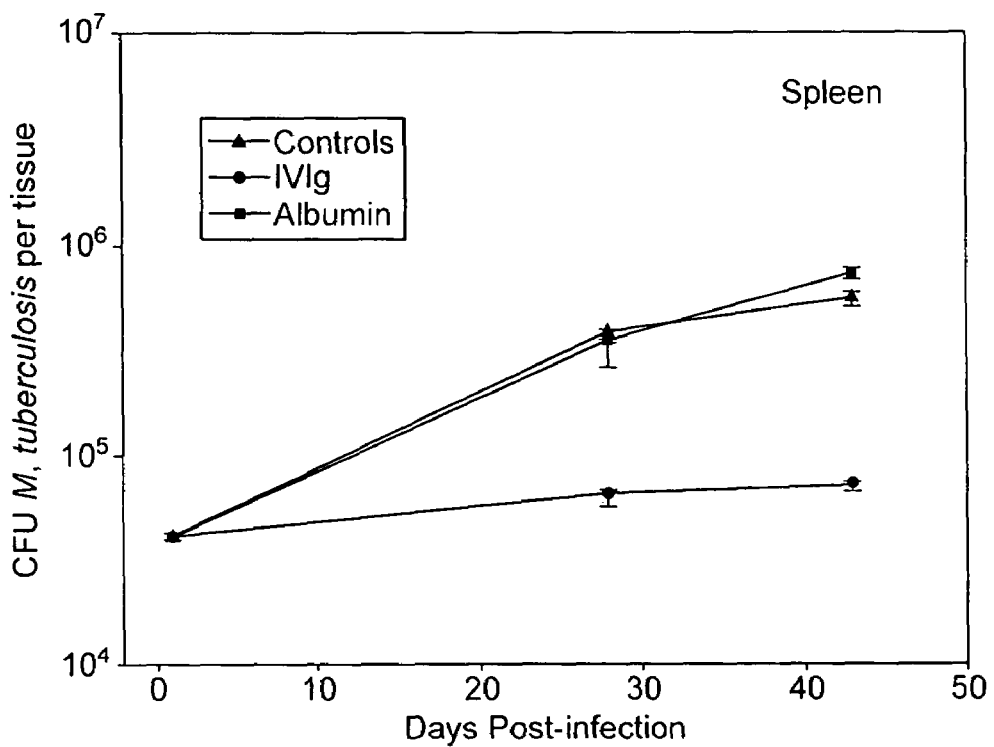
Figure 5:
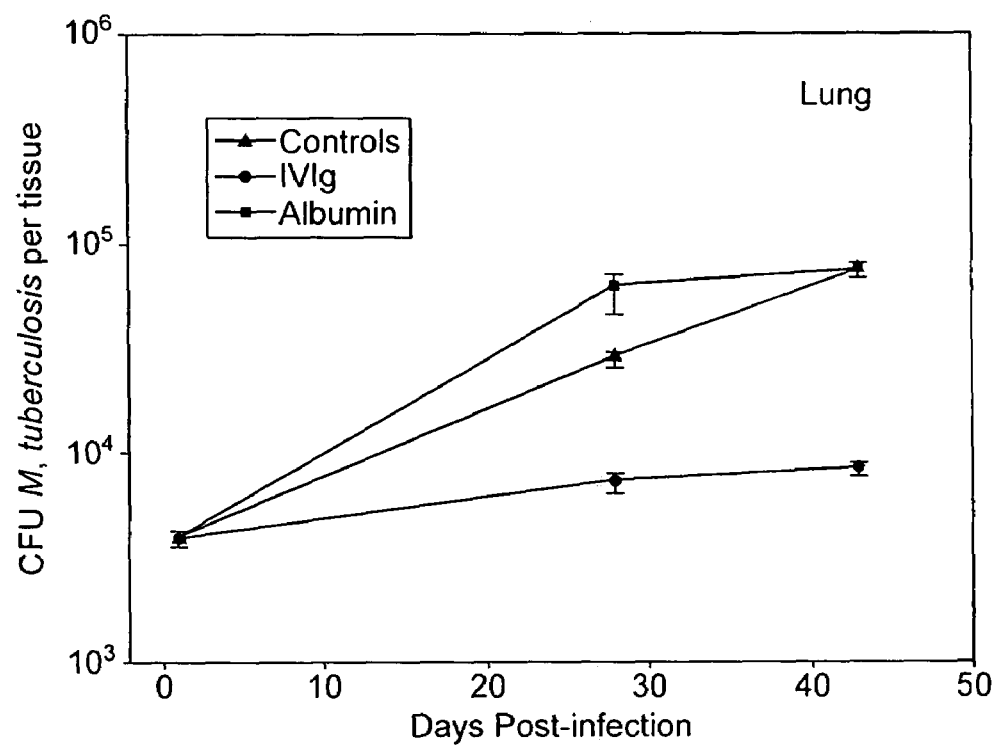
Figure 6:
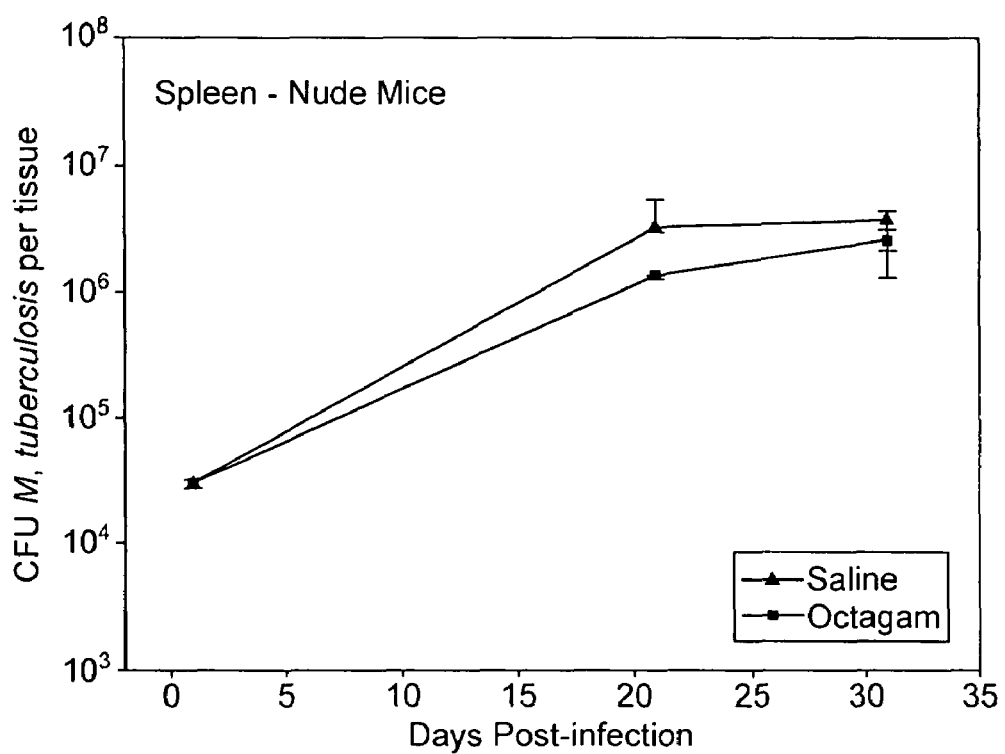
Figure 6:
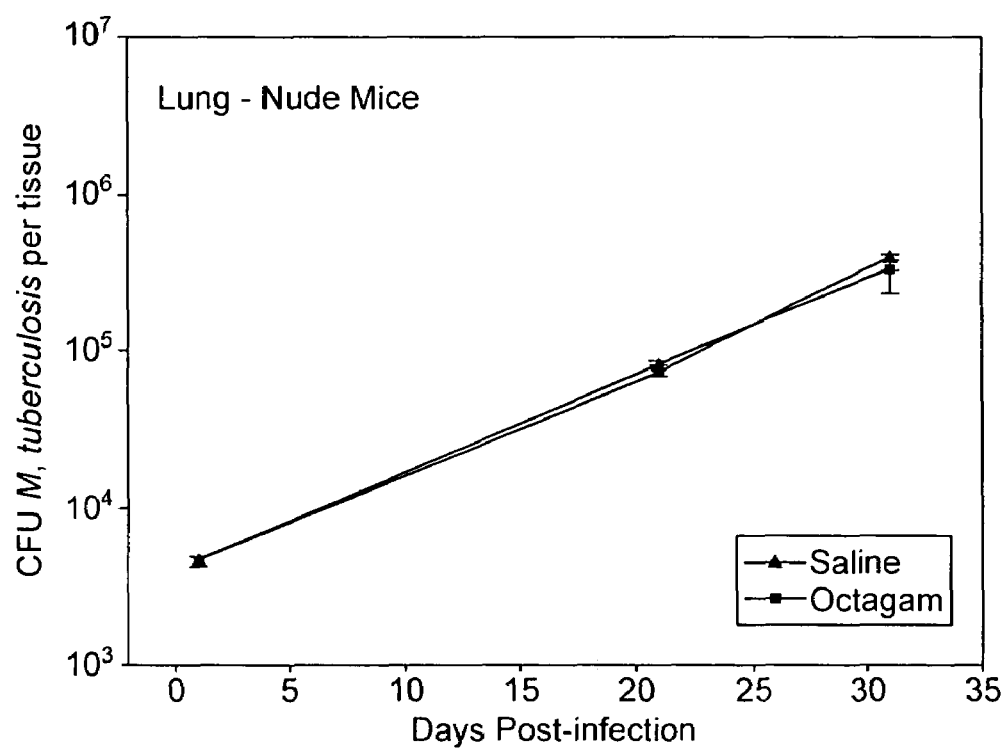
Figure 7:
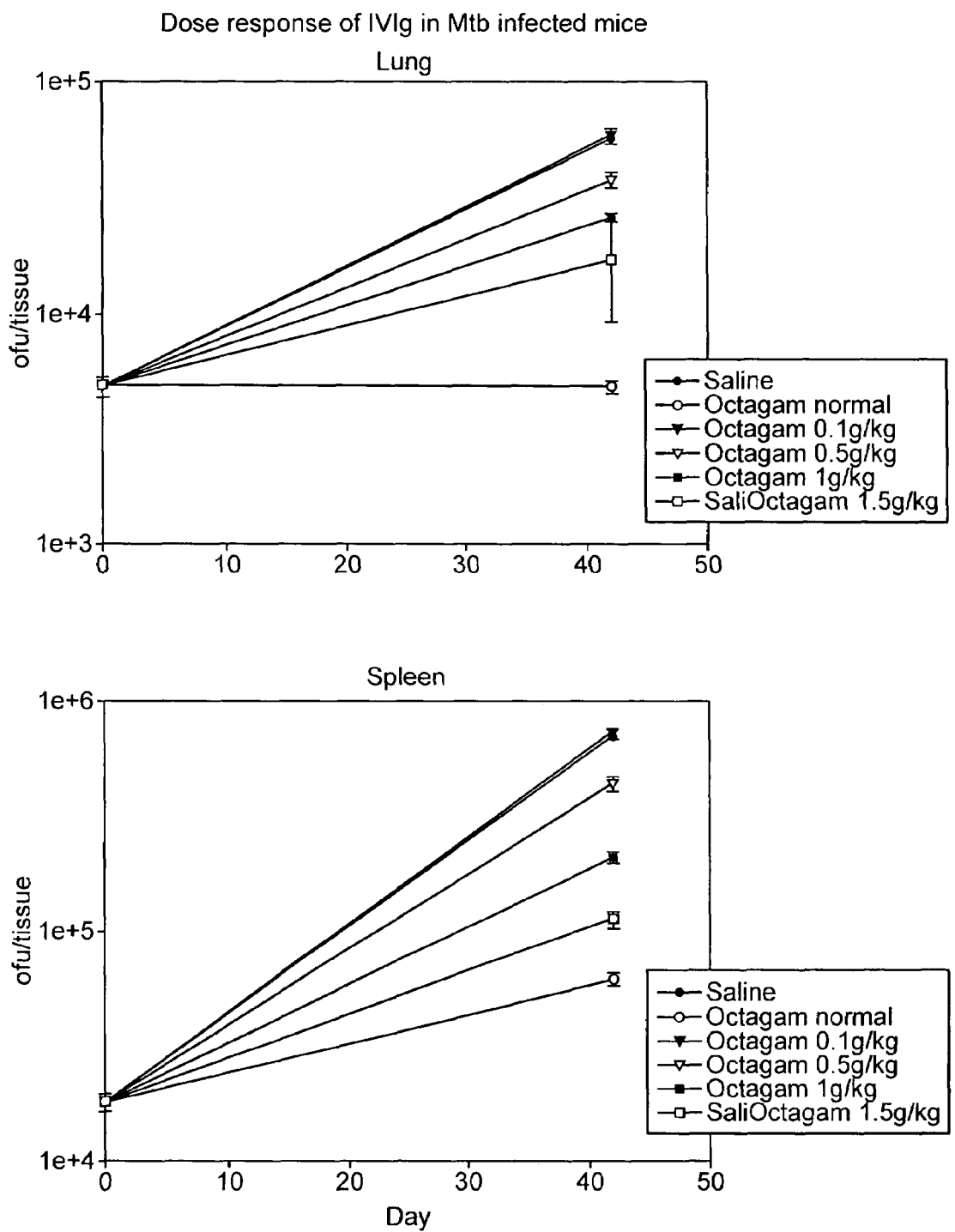

This application is a Continuation that claims priority under 35 U.S.C. §120 to International Application serial no. PCT/GB2004/003830, filed Sep. 8, 2004, which claims priority to GB0320987.1, filed Sep. 8, 2003, GB0322288.2, filed Sep. 23, 2003, and GB0402358.6, filed Feb. 3, 2004, the contents of which are hereby incorporated by reference in their entirety.

The present invention relates to the treatment and/or prophylaxis of tuberculosis. In particular, the invention relates to the treatment or prophylaxis of *Mycobacterium tuberculosis* infection by the administration of plasma immunoglobulin.

Infection with *Mycobacterium tuberculosis* is a major global health problem with one third of the world's population infected. There is only one licensed vaccine (BCG) with variable efficacy. In view of the global seriousness of the problem, the World Health Organisation declared it to be a Global Emergency in 1993. Two million people die every year, constituting 26% of avoidable adult deaths world-wide.

Plasma immunoglobulin is a blood product prepared from the serum of between 1000-15000 donors per batch, and referred to as intravenous immunoglobulin (IVIg), subcutaneous immunoglobulin (SCIg) or intramuscular immunoglobulin (IMIg) according to the specific formulation relating to the intended route of administration. Functionally, IVIg, SCIg and IMIg are equivalent. These immunoglobulins are the treatment of choice for patients with antibody deficiencies. In this indication, IVIg is used at a 'replacement dose' of 200-400 mg/kg body weight, given approximately three weekly. In contrast, 'high dose' IVIg (hdIVIg), given most frequently at 2 g/kg/month, is used as an 'immunomodulatory' agent in an increasing number of immune and inflammatory disorders (1).

Plasma immunoglobulin may be considered to have four separate mechanistic components:

1) actions mediated by the variable regions F(ab')$_2$;
2) actions of Fc on a range of Fc receptors (FcR);
3) actions mediated by complement binding within the Fc fragment; and
4) immunomodulatory substances other than antibody in the plasma preparations.

It is likely that these components, however different mechanisms may be important in different settings. In some cases more than one mechanisms is operative or current understanding does not allow accurate categorisation.

SUMMARY OF THE INVENTION

We have found that subjects treated with hdIVIg following infection with *M. tuberculosis* have significantly lower colony counts in the lungs and spleen; and moreover that IVIg in vitro does not inhibit the growth of TB in macrophages. These results indicate that IVIg improves the immunological response to *M. tuberculosis.*

According to a first aspect of the invention, therefore, there is provided the use of intravenous immunoglobulin (IVIg), subcutaneous immunoglobulin (SCIg) or intramuscular immunoglobulin (IMIg) in the preparation of a medicament for the treatment and/or prophylaxis of mycobacterial infection.

Preferably, the mycobacterial infection is *M. tuberculosis* infection. The medicament according to the invention is advantageously administered to subject(s) suffering from or at risk from tuberculosis.

Intravenous immunoglobulin (IVIg), subcutaneous immunoglobulin (SCIg) or intramuscular immunoglobulin (IMIg) are functionally equivalent and referred to herein, for convenience, as IVIg. In a preferred embodiment, the plasma immunoglobulin referred to herein as IVIg is administered intravenously and is intravenous immunoglobulin.

Advantageously, the IVIg is human IVIg and preferably comprises about 90% IgG, preferably about 95% IgG. Suitable IVIg preparations are known in the art (see Table 1), and include OCTAGAM® and GAMMANORM® manufactured by Octapharma, Vienna, Austria. IVIg preparations known in the art are indicated for and licensed for administration in conditions of immunodeficiency, such as CVID, XLA, Wiskoot Aldrich syndrome, as well as for their immunomodulatory properties, for example in Guillain Barré syndrome.

IVIg Immunoglobulin may be administered intramuscularly, intravenously, subcutaneously or nebulised, though it is more usually given intravenously. For example, a vein may be catheterised for the administration procedure.

IVIg may also be administered subcutaneously. This method of administration is used less frequently and can cause discomfort at the site. Some IVIg prescriptions may be ordered at slower rates continuously over several days. The subcutaneous method is better suited for these slower rates to maintain the Ig level. However, this method is generally not suitable for high dose administration.

Because of the large doses required for immunomodulation, high dose IVIg usually is given intravenously over several hours, typically for several consecutive days. A typical course of therapy may require 2-6 hours infusions for 4-5 consecutive days.

For treatment and/or prophylaxis of TB, IVIg is advantageously administered at a "high dose", that is at a dose superior to the replacement dose. Replacement dose is typically 200-400 mg/kg, given three-weekly. Typically, high dose IVIg is given at at least 1 g/kg/month, and advantageously about 2 g/kg/month. High-dose administration is associated with immunomodulatory use of IVIg, for example as indicated for Guillain-Barré syndrome, where a dose of 0.4 g/kg/day for 3-7 days is advocated.

The invention moreover provides a method for treating a mycobacterial infection in a subject in need thereof, comprising administering to said subject intravenous immunoglobulin (IVIg).

Further, the invention provides a method for preventing a mycobacterial infection in a subject, comprising administering to said subject intravenous immunoglobulin (IVIg).

Advantageously, the mycobacterial infection is *M. tuberculosis* infection.

In a further embodiment, the invention provides IVIg and a vaccine for combined use in the treatment or prevention of infection. Thus, the invention provides IVIg and a vaccine for simultaneous, simultaneous separate or sequential use in the treatment or prevention of infection.

Although not wishing to be bound by theory, the effect of IVIg on the immune response to *M. tuberculosis* infection may be seen in terms of a cross-priming phenomenon, in which macrophages infected by *M. tuberculosis* cross-prime dendritic cells (DCs) or professional antigen presenting cells (APCs), for example through apoptosis of the macrophages and blebbing of vesicles comprising *M. tuberculosis* bacilli, proteins derived from *M. tuberculosis* or surface components of *M. tuberculosis*-infected cells. Uptake of vesicles or macrophages by DCs may be enhanced through interaction between Fc receptors (FcR) on DCs and antibodies present in IVIg which are specific for the *M. tuberculosis*-related components present therein. The DCs or APCs thus cross-primed are able to initiate a CD4+ and/or CD8+ T-cell response against *M. tuberculosis*.

A similar approach is of benefit in other infectious diseases (e.g. leprosy etc) and tumours which require a T cell mediated immune response which can be augmented by improved cross priming.

Accordingly, the invention provides the use of IVIg to potentiate the use of any vaccine. The invention is particularly indicated for use against intracellular infectious organisms, which may evade DCs and APCs though multiplying in different cell types. Advantageously, therefore, the vaccine is a vaccine against an intracellular infectious organism.

The vaccine may be a conventional vaccine based on killed, attenuated or similar organisms; in the case of TB, the vaccine may be the BCG (Bacillus Calmette-Guérin) vaccine, a DNA vaccine, a recombinant protein or subunit vaccine, or the like.

It is possible to deliver intact IgG into the lungs using a nebuliser (Aerogen Inc. Mountain View, Calif., USA) which does not destroy the function of the IgG protein. Given that *M. tuberculosis* is spread via the respiratory route and the majority of infections are pulmonary it may be advantageous to deliver IVIg into the lungs to enhance the immune response locally.

Moreover, pulmonary delivery of vaccines, such as the BCG TB vaccine, may be combined with pulmonary delivery of IVIg to provide a potentiated vaccine for uptake via the pulmonary route. Typically, lower doses of IVIg are sufficient when delivered by the pulmonary route.

Where the IVIg is acting to facilitate cross-priming of DCs and/or APCs, the IVIg may be replaced with a more specific immunoglobulin preparation. For example, immune serum from BCG-vaccinated or DNA-vaccinated individuals, or a polyclonal or monoclonal anti-*M. tuberculosis* IgG may be used to facilitate uptake of blebbed macrophage vesicles by FcR on DCs or APCs. More specific Ig preparations are especially suited to pulmonary delivery as described above.

Where immunoglobulin preparations are used which are more specific than IVIg, the dose used may be lowered with respect to the standard IVIg dose. For example, doses of 0.1-1 μg/kg, 1-10 μg/kg, 10-100 μg/kg or more are envisaged, administered over a period of one to several days in a series of repeated administrations.

DESCRIPTION OF THE FIGURES

FIG. 1. The effect of IVIg on the growth of *M. tuberculosis* in macrophages.

Murine C57BL/6 bone marrow derived macrophages are infected with *M. tuberculosis* for 6 hours, washed and maintained in either control medium or medium containing IVIg. Colony counts were obtained on days 0, 3 and 6. There was no difference in colony counts between the groups.

FIG. 2. The effect of IVIg on the growth of *M. tuberculosis* in mice.

Colony counts of *M. tuberculosis* in the spleens and lungs taken from animals at different time points show a significant reduction in IVIg treated animals compared to controls. This effect seems to increase over time and is slightly greater in mice treated with IVIg on days 3 and 5 post infection. Each point represents five mice and error bars are standard error of the mean.

FIG. 3. Lung Histology.

Lung sections of control and IVIg treated mice at 40× and 100× magnification stained with haematoxylin and eosin at day 42 following infection. The lungs obtained from IVIg treated mice contain granulomata which compared to controls, exhibit a considerably more dense lymphocytic infiltrate, while the ratio of macrophages to lymphocytes is greater in controls. This suggests a more vigorous immunological response in the treated animals.

FIG. 4 Late Treatment

Colony counts of *M. tuberculosis* in the spleens and lungs taken from animals at different time points show that late treatment of animals by injection of octagam 105 days post-infection effectively reduces the *M. tuberculosis* load to that seen when the animals are treated at an early stage. This suggests an effective therapeutic outcome with IVIg treatment.

FIG. 5. Control with Albumin

Colony counts of *M. tuberculosis* in the spleens and lungs taken from animals at different time points show that human albumin has no effect. This confirms that the observed phenomenon is not related to a mouse anti-human response.

FIG. 6. The effect of IVIg in Nude Mice Infected with Mtb.

Colony counts were obtained from the lungs and spleens of control or IVIg treated nude mice. Each point represents 5 mice and the experiment was repeated twice. There is no difference in the colony counts between control and IVIg treated nude mice, suggesting that the mechanism of action of IVIg may act through T cells.

FIG. 7. Dose Response of IVIg in Mtb infected Mice.

Mice were infected with Mtb and treated with saline control, 0.1 g/kg, 0.5 g/kg, 1 g/kg, 1.5 g/kg or 2 g/kg of IVIg and colony counts obtained from the lungs and spleens. Each point represents five mice and error bars are standard error of the mean. The results show that the greater reduction in colony counts was achieved with a dose of 2 g/kg.

DETAILED DESCRIPTION OF THE INVENTION

IVIg, as defined herein, is a plasma product comprising pooled plasma from at least two individuals and comprising at least about 90% IgG. Advantageously, it is prepared from the pooled plasma of 1000 or more individuals. IVIg is by its nature highly polyclonal, and comprises many antibody specificities, as well as non-antibody immunoactive molecules such as cytokines. The term "IVIg" includes intravenous immunoglobulin (IVIg), subcutaneous immunoglobulins (SCIg) and intramascular immunoglobulin (IMIg).

Treatment, as defined herein, is the modulation of an existing condition such as the attenuation of an existing infection. Thus, the treatment of a mycobacterial infection by the administration of IVIg presupposes that the subject to be treated has a mycobacterial infection prior to the said administration. In an experimental context, an infection is "treated" as described herein if the titre of the infectious organism is reduced by a factor of 10 in the subject, and preferably a factor of 100 or more. Titre can be assayed by a standard colony formation assays for *M. tuberculosis*. In the context of therapy, an invention is "treated" is a measurable microbiological or therapeutic benefit observable in the patient.

Prevention or prophylaxis is the inhibition of attenuation of an infection acquired after the administration of the treatment. Thus, if a subject becomes infected with *M. tuberculosis* subsequent to treatment with IVIg, and optionally BCG, DNA or other vaccine, attenuation or prevention of the infection is observed. In an experimental context, an infection is "attenuated" as described herein if the titre of the infectious organism is reduced by a factor of 10 in the subject, and preferably a factor of 100 or more. Titre can be assayed by a standard colony formation assays for *M. tuberculosis*. In a therapeutic context, attenuation is defined in terms of a measurable microbiological or therapeutic benefit in the patient.

Vaccine as referred to herein is a preparation which elicits immunological protection against a pathogen. Preferably, the pathogen is an intracellular organism. The vaccine may be a conventional vaccine, that is a vaccine consisting of non-pathogenic organisms which are homologous with the potential pathogen, or attenuated and/or killed pathogens, which elicit an immune response due to the presence of antigens similar or identical to those of the pathogen, but without the pathogenic effects. Alternatively, it may be a DNA vaccine, which comprises a DNA molecule encoding one or more antigenic epitopes characteristic of the pathogen, or a peptide or subunit vaccine which comprises peptide or protein components characteristic the pathogen. Typically, such components may be produced recombinantly.

Intracellular organism, when applied to pathogens herein, denotes that the organism is present within the cells of the infected individual. Generally, it is not present outside said cells and effectively "hides" from the immune system by concealing itself within infected cells.

Mice.

C57BL/6 and BALB/c mice aged 8-12 weeks obtained from the SPF and NIMR were used throughout these studies.

*M. tuberculosis* Culture for Intravenous Infections.

A 250 ml Dubos containing 10 ml of albumin Dubos supplement (Difco, Laboratories, Surrey, United Kingdom) was inoculated with 1 ml of TB culture obtained from original stock and incubated in a 37° C. rotating incubator for five days. The OD reading at 600 nm found to be 0.380. This was diluted to an OD of 0.02 in saline.

Intravenous Infections of Mice

Mice were held in a restraining box. The tail of the mouse was warmed with a heat lamp and swabbed with gauze soaked in 70% ethanol. A 1 ml syringe with a 25-G needle was filled with the innoculum and any air bubbles removed. The lateral tail vein was visualised and the needle was inserted parallel to the vein 2 to 4 mm into the human. Each mouse received 0.2 ml of TB of concentration $2.00\times10^5$.

The infection was monitored by removing the lungs and spleens of infected mice at various intervals; the baseline level of infection of each tissue was estimated by harvesting organs from the mice 18 h after infection and determining viable counts. The tissues were weighed and homogenised by shaking with 2-mm-diameter glass beads in chilled saline with a Mini-Bread Beater (Biospec Products, Bartleville, Okla.), and 10-fold dilutions of the suspension were plated onto Dubos 7H11 agar with Dubos oleic albumic complex supplement (Difco Laboratories, Surrey, United Kingdom). Numbers of CFU were determined after the plates had been incubated at 37° C. for approximately 20 days.

Intraperitoneal Administration of Compounds in Mice

The mouse was restrained manually. A 1 ml syringe with a 22-G needle was filled with Octagam 5% liquid and any air bubbles were removed. The needle then was inserted into the lower right quadrant of the abdomen, avoiding the abdomen midline and 0.5 ml injected into each mouse 6 hours post infection and repeated on day 2.

Generation of Bone Marrow Derived Macrophages.

Media 500 ml Iscoves modified Dulbeccos medium (IMDM), 5% (25 ml) heat-inactivated FCS, 2 mM L-glutamine, 50 uM 2-mercaptoethanol, 10% L929 cell supernatant (source of M-CSF).

On Day 0 bone marrow from C57BI/6 mice was removed. Cells were washed counted and resuspended to $2\times10^6$ cells/ml in cIMDM with 10% L929 cell supernatant. The cells were plated into 12 well plates at 1 ml/well and incubated at 37° C. On day 3 the non-adherent cells and medium were removed and fresh medium containing 10% L929 cell supernatant added. This was repeated on day 5 and the cells infected on day 6.

Growth of H37Rv in Bone Marrow Derived Macrophages.

Macrophages were grown in 12 well plates, 1 plate per day for day 0, 4, 7, 9, & 11. Each plate contained 8 wells (1 ml/well) 4 control wells and 4 IVIg treated wells (AMMANORM). Medium was cIMDM with 10% L929 cell supernatant containing either 25 mg/ml IVIg or saline. Human albumin (Sigma-Aldrich, St. Louis, Mo.) was used as a control.

On day 0 the number of macrophages per well was counted and all wells infected with H37Rv at multiplicity of infection (MOI) 2:1 and incubated at 37° C. for 6 hrs in medium not containing IVIg. Following this the medium was removed and replaced with fresh cIMDM containing either 25 mg/ml IVIg or human albumin control. Four plates were returned to the incubator and day 0 colony forming units (cfu) performed to establish a base line for growth.

Preparation of CFU Plates.

The supernatant was removed from each well and retained. Each well was washed three times with 1 ml PBS and 1 ml PBS with 100 ul 2% saponin added to each well, and incubated at 37° C. for a minimum of 1 hr.

1 in 10 serial dilutions of each well and each supernatant were prepared in 900 ul saline to 10-4, (neat, 10, 100, 1000, 10000 fold dilutions). 20 ul of each dilution was applied to 7H11 plates with albumin, these were divided into 5 sections (duplicate plate per well/supernatant), allowed to dry, wrapped, inverted and incubated at 37° C. for 14-21 days before counting (no colonies×dilution factor=cfu/ml).

The Effects of IVIg on Protective Response to DNA Vaccination Against TB Challenge.

Seven groups of 8 Balb/c females, 6-8 wk

Group 1: Given 0.5 ml IVIg (CTAGAM) injected ip then 9 h later given 50 µl DNA injected into the muscle tissue of each hind leg (100 µl total). The DNA was 1 mg/ml plasmid in buffered saline, expressing mycobacterial hsp65 from CMV immediate early gene promoter (2-4). 24 h after the first dose of IVIg they received another 0.5 ml IVIg ip. Then 21d and 42d after the first DNA injections the mice were challenged by iv injection of *M. tuberculosis* H37Rv. Four weeks after infection, mice were killed for counts of live bacteria in lungs and spleens.

Group 2: As above but the dose of IVIg was reduced to 0.2 ml instead of 1 ml total.

Group 3: High dose IVIg as in Group 1 but without DNA

Group 4: Low dose IVIg as in Group 2 but without DNA.

Group 5: Untreated controls.

Group 6: DNA treatment as in Group 1 but without IVIg treatment.

Group 7: BCG vaccinated, 50 µl so at the time of first IVIg treatment.

Statistics.

Data are the geometric means and the standard errors of the means of five mice. Graphs were plotted using SigmaPlot 8.0 software.

Antibodies and Reagents.

Staining of cells obtained from lungs was performed using directly conjugated anti TCR PB, anti CD4 FITC, anti CD8 FITC, anti CD44 PE and anti IFNγPE from Pharmingen.

Therapeutic Intravenous Immunoglobulin.

CTAGAM and AMMANORM (Octapharma, Vienna, Austria) both pooled normal IgG obtained from healthy donors were used. CTAGAM was used for the in vivo experiments unaltered and AMMANORM for the in vitro studies. The AMMANORM was dialysed twice in either rRPMI 1640 (Gibco) or IMDM (Gibco) before use to remove stabilizing agents and filter sterilized, or used unaltered.

Lung Histology.

Mice were given a lethal dose of anaesthetic (Sagatal) i.p.; the lungs fused with 1 ml 10% neutral buffered formalin solution (Sigma) via the trachea in situ and a further 1 ml on removal of the lungs before being placed in 10 ml 10% neutral buffered formalin for 3 days to await histology. After dehydration in a graded series of ethanol and clearing in xylene, the lungs were embedded in fibrowax (BDH). Sections of 6 µm thickness were stained with haematoxylin and eosin. For immunohistochemical localisation of iNOS, serial lung sections were deparaffinized and incubated with 0.1 µg/ml of rabbit anti-mouse iNOS (BD Transduction Laboratories). Bound antibodies were detected with biotylated, affinity-purified anti-rabbit immunoglobulin as the secondary antibody, and after washing, the sections were incubated with avidin-coupled biotinylated horseradish peoxidase with aminobenzidine as substrate (VECTASTAIN ABS Kit, VECTOR Laboratories) according to the manufacturer's instructions.

Results

Administration of human pooled IVIg to mice following infection with *Mycobacterium tuberculosis* reduced the colony counts in lungs and spleen by 1000 fold and was associated with a more lymphocyte predominant appearance of lung granulomas than in control mice. When IVIg was given on days three and five following infection rather than 6 hours and 24 hours the reduction in colony counts was slightly greater. IVIg did not affect the growth of *M. tuberculosis* in murine bone marrow derived macrophages in vitro.

The reduction of *M. tuberculosis* colony counts when IVIg was given on days three and five post infection suggests that it is unlikely that *M. tuberculosis* being opsonised and killed in the circulation as the organism becomes intracellular within hours following infection. In support of this is the fact that the difference in the colony counts from control increases with time and at a time when there would have been a mouse anti human response. Taken with the lack of effect of IVIg on the growth of *M. tuberculosis* in macrophages in vitro this suggests that the improved control of infection is immunological in nature. The lung histology shows a more lymphocytic infiltrate within granulomas in treated mice.

The mechanisms of action of IVIg given at immunomodulatory doses are complex and incompletely understood. The possibilities for the benefit observed in mice infected with *M. tuberculosis* may be divided into two major subsets based on the structure of the antibody molecule and are mechanisms dependent on Fc or the variable binding site regions of F(ab)$_2$. It would be possible to test the role of Fc interactions in a number of ways. Fc could be given alone having digested F(ab)$_2$ using papain as a control or monoclonal human myeloma IgG1 could be used as this would have only one binding specificity and therefore not reflect the repertoire present in polyclonal IVIg. The avidity of an Fc reagent could be increased to enhance this modality using Fc tetramers. Another possibility would be the use of pre-treatment with anti murine Fc to block Fc interactions. These approaches might delineate which part of the antibody molecule was most important. Fc interactions through FcRγIIB, which delivers a negative signal through an ITIM motif have been shown to downregulate macrophage function (5). It has also been shown that IVIg inhibits dendritio cell maturation (6) and this may be important as immature DCs have an antigen sampling role while mature DCs loose this ability and become functionally more potent antigen presenting cells. Cross priming is an important mechanism for antigen presentation in mycobacterial infection (7), if the action of IVIg is through enhancement of cross priming it would be beneficial to temporarily maintain DCs in an immature state in which they were able to take up antigen and for these two events to coincide. It has been shown that cross priming using antibody immune complex coated apoptotic tumour cells enhances anti tumour immunity and tumour rejection (8). A further potential immunomodulatory mechanism might be to alter the numbers of regulatory T cells (CD4 CD25, IL-10) present which have been shown in a Leishmania model to allow persistence of infection.

It would be possible to determine if particular F(ab)$_2$ variable region binding site interactions are important. The serum of mice treated with DNA vaccination, BCG, or *M. tuberculosis* could be used to augment vaccination with DNA or BCG. These interactions may play a role in cross priming which has been shown to be important for protection against *M. tuberculosis*.

The data suggest a novel means by which t enhance the immune response to *M. tuberculosis* using an agent, which is already licensed for human use. The IVIg used (CTAGAM) is produced from plasma derived from donors in Austria, Germany and the US and will contain antibodies from BCG vaccinated individuals. It has been shown that the efficacy of BCG given in trials in parts of south India and southern Africa has little benefit (9, 10) while in most cases in the developed world there has been demonstrable efficacy. This has been explained by differences in environmental factors such as prior exposure to other environmental mycobacteria in parts of south India and southern Africa. It is possible that IVIg imposes a western antibody binding site repertoire, which facilitates the response to *M. tuberculosis* and potentially even vaccination efficacy in mice maintained in an SPF environment.

All publications mentioned in the present specification are here incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the following claims.

REFERENCES

1. Sewell W A, Jolles S. Immunomodulatory action of intravenous immunoglobulin. Immunology 2002; 107:387-93.
2. Tascon R E, Colston M J, Ragno S, Stavropoulos B, Gregory D, Lowrie D B, Vaccination against tuberculosis by DNA injection. Nat Med 1996; 2:888-92.
3. Lowrie D B, Tascon R E, Bonato V L, Lima V M, Faccioli L H, Stavropoulos E, et al. Therapy of tuberculosis in mice by DNA vaccination. Nature 1999; 400:269-71.
4. Lowrie D B DNA vaccines against tuberculosis. Curr Opin Mol Ther 1999; 1:30-3.
5. Samuelson A, Towers T L, Ravetch J V. Anti-inflammatory activity of IVIg mediated through the inhibitory Fc receptor. Science 2001; 291:484-6.

6. Bayry J, Lacroix-Desmazes S, Carbonnell C, Misra N, Donkova V, Pashov A, et al. Inhibition of maturation and function of dendritic cells by intravenous immunoglobulin. Blood 2003; 101:758-65.
7. Schaible U E, Winan F, Sieling P A, Fischer K, Collins H L, Hagens K, et al. Apoptosis facilitates antigen presentation to T Lymphocytes through MHC-I and CD1 in tuberculosis. Nat Med 2003; 9:1039-46.
8. Akiyama K, Ebihara S, Yada A, Matsummura K, Aiba S, Nukiwa T, et al. Targeting apoptotic tumor cells to Fc gamma R provides efficient and versatile vaccination against tumors by dendritic cells. J. Immunol 2003; 170: 1641-8.
9. Fine P, Group K P T. Randomised controlled trial of single BCG, repeated BCG, or combined BCG and killed Mycobacterium leprae vaccine for prevention of leprosy and tuberculosis in Malawi. Karonga Prevention Trial Group. Lancet 1996; 348:17-24.
10. Tripathy S P. Trial of BCG vaccines in South India for tuberculosis prevention: First Report Bulletin of the World Health Organization 1979; 57:819-827.

TABLE 1

IGIV INFORMATION CHART

| PRODUCT | Aventis | Novartis/AmRed Cross | Aventis | Immune | Aventis | Baxter/Hyland | PRODUCT |
|---|---|---|---|---|---|---|---|
| | Behring | ZLB/CSL Sandoglobulin | Bohring | Baxter | Behring | Am.Red Cross | |
| Name(s) | Gamma-Venin P | Panglobulin Careimune | Venimmun | Endobulin | Gammar IVP | Gammagard SD | Names(s) |
| Manufactured in | Germany | Switzerland | Germany | Austria | USA | USA/Belgium | Country of Manuf |
| Process | Cohn | IGstier-Nitschmann pH4, pepsin nanofiltration | Cohn Sulfilolysis | Cohn PEG | Cohn pH4 | Cohn DEAE Sephadax PEG | Process |
| Plasma Source | German | US/Swiss | German | US/Aus/Ger | US | US | Plasma Source |
| Type | 5s | 7s | 7s | 7s | 7s | 7s | Plasma Type |
| Form | powder | powder | powder | powder | powder | powder | Form |
| Viral Inactivation | Pastereurized | pH4 | Past. | 9D | Past | SD | Viral Inactivation |
| Concentration | 5% | 3-12% | 5% | 5% | 5-10% | 5-10% | Concentration |
| Half-Life (days) | 12-36 hours | 30 | 21-36 | 27 | 22 | 24 | Half-Life (days) |
| % IgG | >95 | >95 | >85 | >99 | >98 | >98 | %IgG |
| IgG1 % | | 65.2 | 65 | 60-70 | 69 | 71.2 | IgG1 % |
| IgG2 % | | 28.3 | 25 | 30-40 | 23 | 21.3 | IgG2 % |
| IgG3 % | | 4.15 | 5 | 0.8 | 6 | 4.5 | IgG3 % |
| IgG4 % | | 2.4 | 5 | 2 | 2 | 3.1 | IgG4 % |
| % Monomers | >95 | 86 | >80 | <93 | >90 | >90 | % Monomers |
| % Dimers | | >4% | >10% | | | | % Dimers |
| IgA (mg/mL) | | 1.2 | 5 | 0.06 | <0.1 | <0.003 | IgA (mg/mL) |
| IgM (mg/mL) | | <0.1 | | <0.1 | <0.1 | <0.1 | IgM (mg/mL) |
| Sodium (mg/ml) | 8.5 | 9 | 8.5 | 3 | 5 | 8 | Sodium (mg/mL) |
| Sugar/Stabilizer | Glycine | Sucrose | Glycine | Glucose | Glucose | Glucose/glycine | Sugar/Stabilizer |
| Osmotality | | 680-1074 (NaCl) | | 357 | | | Osmotality |
| Albumin Content | none | 3% | none | 7 | 8.0 mg/mL | 3 | Albumin Content |
| pH | 5.8 | 6.6 | 6.8 | 7 | 7 | 7 | pH |
| Anti-A | | | | | | 1:4 | Anti-A |
| Anti-B | | | | | | 1:5 | Anti-B |
| Anti-D | | | | | | | Anti-D |
| Pkg. Sizes | 0.25/0.5/2.5/5/10 | 1/3/6/12 | 0.5/2.5/5/10 | 0.25/0.5/1 | 0.5/2.5/5/10 2.5/5/7.5/10 | 0.5/2.5/5/10 | Pkg. Sizes |
| Shelf-Life (mths) | 24 | 36 | 24 | 24 | 24 | 24 | Shelf-Life (mths) |
| Storage | Room Temp | Room Temp | Room-Temp | Refrigerate | Room Temp | Room Temp | Storage |
| Solubility | | 20 minutes | | | | 3-10 min | |
| Max Infusion Rate | 2-3 ml/min | 2.5 ml/min | 2 ml/min | 0.33 ml/kg/min | 2.5 ml/min | 0.13 ml/kg/min | Max. Infusion Rate |
| Registration notes | only Germany | worldwide | Germ/Aust | Aust/Germ Italy | USA Switz/USA | worldwide | Registration notes |
| Inf. Source Promotional Material | German | French | German | Intl Eng | US | Intl English | Inform. Source |
| Bayer/Miles Tropan | Bayer | Octapharma | Bioventrum | BPL | Biotast | PRODUCT | Biotest |

TABLE 1-continued

IGIV INFORMATION CHART

| Property | Polyglobin 5% / Gamimune 5% | Polyglobin 10% / Gamimune 10% | OCTA-GAM | Gammo Nativ N | Viagam-S | Intraglobin F | Intreglobin CP (chrom. purified) |
|---|---|---|---|---|---|---|---|
| Country of Manuf. | USA | USA | Austria | Sweden | UK | Germany | Germany |
| Process | Cohn | Cohn-Oncley | Cohn | Cohn | Cohn | Cohn | Chromatography |
| (purification) | pH4 | pH4 Incubation S/D | pH4 | DEAE Sephadax | Ion Exchange | B-proplolactone | B-proplolactone |
| Plasma Source | US | USA | Aus/Ger/US | Sweden | USA | US/Aus/Ger | US/Aus/Ger |
| Typa | 7s | 7s | 7s | 7s | 7s | 7s | 7s |
| Form | liquid | liquid | liquid | powder | powder | liquid | liquid |
| Viral Inactivation | SD/pH4 | SD,pH4,LpH | SD,pH4 | SD | S/D | B-prop./Nanofittr. | B-prop/9D/Filtration |
| Concentration | 5% | 10% | 5% | 5% | 5% | 5% | 5% |
| Half-Life (days) | 26.4 | >21 days | 28 | 20-25 |  | 21,6 | 22 |
| %IgG | 98% | >98% | >99 |  | >98 | >95 | >95 |
| IgG1 % | 64.6 | 63.2 | 63 | 60.9 | 51.7 | 59.6 | 59 |
| IgG2 % | 28.6 | 29.6 | 28.5 | 35.2 | 40.9 | 36.6 | 38 |
| IgG3 % | 5.7 | 5.7 | 6.3 | 3 | 6.4 | 0.4 | 3 |
| IgG4 % | 1.1 | 1.3 | 2.7 | 0.9 | 1 | 3.4 | 2 |
| % Monomers | >99 | 99 | >92 | 95 | 93.3 |  |  |
| % Dimers |  | 0 | >7% |  |  |  |  |
| IgA (mg/mL) | <0.21 | <0.2 | <0.1 | <0.002 | 5 | 1.5 | <2.5 |
| IgM (mg/mL) | <0.1 | <0.1 | <0.1 | <0.1 | <0.1 | <0.1 | <0.1 |
| Sodium (mg/mL) | 1.2 |  | 0.01 | 9 | 5.9 |  |  |
| Sugar/Stbilizer | Maltose | glycine | Maltose | Glycine/Glucose | sucrose | Glucose | glycine |
| Osmotality | 336 | 261 | >250 <850 | 415 | 340 |  |  |
| Albumin Content | none | none | none | 60 | 20 | none | none |
| pH | 4.2 | 4.25 | 5.5-6.0 | 7 | 6.6 |  |  |
| Anti-A | 1:8 | 01:08 | 1:1 | 1:6 |  |  |  |
| Anti-B | 01:02 | 01:04 | 1:1 | 1:16 |  |  |  |
| Anti-D |  |  | ND |  |  |  |  |
| Pkg. Sizes | 0.5/2.5/5/10 | 1.5.10.20 | 1.0/2.5/5.0/10.0 | 1.5/5 | 1.5/5 | 0.5/1/0/2.5/5.0/10 | 1/2.5/5/10 |
| Shelf-Life (mths) | 24 | 36 | 24 | 36 | 24 | 24 | 36 |
| Storage | Refrigerate | Refrig. | Room Temp. | Refrigerate 8 min | Room Temp | Refrigerate | Refrigerate |
| Max Infusion Rate | 0.08 ml/kg/min | 0.06 ml/kg/min | 3 ml/min | 3 ml/min | 3 ml/min | 2 ml/min |  |
| Registration notes | worldwide | US/Europe | worldwide | Scand/Germ | UK | Germ/Aus/Switz | Germany |
| Inform Source | German Intl | US Pkg. Leaf. German Broch. | Int English | Swedish Intl | UK | German | German |
|  |  |  |  |  |  |  | PEI approved Aug-01 |

| PRODUCT | BPL / Viagam Liquid | Griffols / Alphaglovine / Flabogamma | Alpha / Vanoglobuline S 5% | Alpha / Blavin 10% | Blagini / Narpe(s) | Kadrian Biagini / Islvin / Tegeline | LFS / Biotest | CLB / Intraglobin F |
|---|---|---|---|---|---|---|---|---|
| Country of Manuf. | UK | Spain | USA | US | Italy | Italy | France | Neth |
| Process | Cohn | Cohn | Cohn | Cohn | Cohn | Cohn | Cohn | Cohn |
| (purification) | Ion Exchange pH4 Incub | PEG | PEG | PEG | Ion Exchange | pH4 | pH4/pepsin |  |
| Plasma Source | USA | US/EC | US | US | Italian | Italian | French | Dutch |
| Type | 7s | 7s | 7s | 7s | 7s | 7s | 7s | 7s |
| Form | liquid | liquid | liquid | liquid | powder | powder | powder |  |
| Viral Inactivation | SD,pH4 | Pasteurized | SD/pH4 | SD/pH4 | SD | SD/pH4 | pH4 |  |
| Concentration | 5% | 5% | 5% | 10% | 5% | 5% | 3-12% | 5% |
| Half-Life (days) | 21 | 36-65 | 33.5+/-31 7 |  | 24 | 24 | 24 |  |
| %IgG | 100 | >99 | >99 |  |  | 89 | >97 |  |
| IgG1 % | 56 | 69.7 | 69.7 |  |  | 62-70 | 58.6 |  |
| IgG2 % | 38 | 28.13 | 28.2 |  |  | 20-24 | 34.1 |  |
| IgG3 % | 5.4 | 1.32 | 1.3 |  |  | 8.5-9.4 | 5.4 |  |
| IgG4 % | 0.6 | 0.67 | 0.9 |  |  | 3.8-4.2 | 1.7 |  |

TABLE 1-continued

IGIV INFORMATION CHART

| | | | | | | | | |
|---|---|---|---|---|---|---|---|---|
| 95 | | >94 | | | % Monomers | 0 | | |
| 3.5 | | | | | % Dimers | 100 | | |
| 5 | <0.05 | <0.008 | | 0.1 | IgA (mg/mL) | 0.118 | 0.85 | |
| | <0.1 | <0.1 | | <0.1 | IgM (mg/mL) | 0.1 | <0.1 | |
| 9 mmol/l | | | | 9 | Sodium (mg/mL) | 8.5 | 2 | |
| Sucrose | d-Sorbital | d-Sorbital | d-Sorbital | Sucrose | Sugar/Stabilizer | Sucrose | | Sucrose |
| 400 | | 300 | 330 | | Osmotality | 450-600 | | |
| 2 gms/5 gm via) | | 1.3 | 2.6 | none | Albumin Content | none | | |
| 4.9 | 5.4 | 5.2-6.6 | | 6.8 | pH | 7 | | |
| | | 1:8 | | low | Anti-A | 01:04 | | |
| | | 1:8 | | low | Anti-B | 01:04 | | |
| | | 1:8 | | low | Anti-D | | | |
| 5 | 0.5/2.5/10 | 2.5/5/10 | 5/10/20.0 | 0.5/1/2.5/5 | Pkg. Sizes | 1/2.5/5 | 0.5/2.5/5/10 | |
| 24 | 24 | 24 | 24 | 36 | Shelf-Life (mths) | 36 | 36 | |
| refrig. | Room Temp Refrig in Spain | Room Temp | Refrigerate | Room Temp | Storage | Room Temp | Room Temp | |
| 3 ml/min | | 0.08 ml/kg/min | 0.05 ml/kg/min | | Max Infusion Rate | | 0.067 ml/kg/min | |
| UK | Spain, Port, UK, Germ, Switz | USA | USA | Italy | Registration notes | Italy | France | Nath |
| UK | Spain/Germ Expanding registrations in export countries, USA, Portugal | US sorbital can not be used for fructose intolerance | US | Turkish | Inform. Source | Turkish | French | |
| BRC See Biotest Intraglobin F | Finnish Red Cross | Human Humaglobin | CSL Intragam | PRODUCT Name(s) Gammareas | Shanghai Reas | CBSF/ (Yung Shin Pharm) see Sandoglobin | Normal Plasma Gamurax | Baxter self Sufficiency |
| Beig | Finland Cohn pH4/pepsin | Hungary Cohn PEG | Australia Cohn/Column | Country of Manuf. Process | China Cohn | Taiwan | | |
| Beig | Finnish 7s liquid SD/Nanofir | Hungary 7s Powder Haal | Australia 7s liquid unknown | Plasma Source Type Form Viral Inactivation | China 7s liquid double | Taiwan 7s powder | | |
| 5% | 5% | 5% | 8% | Concentration Half-Life (days) | 5% | 3% | | |
| | | 22 | | | | | | |
| | | >95 | 21-42 | % IgG | | | | |
| | | 66 | | IgG1 % | | | 60-70 | |
| | | 29 | | IgG2 % | | | 15-25 | |
| | | 1 | | IgG3 % | | | 4.0-6 | |
| | | 2 | | IgG4 % | | | 2.0-6 | |
| | | | >90 | % Monomers | | | | |
| | | | | % Dimers | | | | |
| | | <0.5 | | IgA (mg/mL) | <0.12 | | | |
| | | | | IgM (mg/mL) | | | | |
| | | | | Sodium (mg/mL) | | | | |
| | | glucose/glycin | Maltose | Sugar/Stabilizer | | | | |
| | | >240 | | Osmotality | | | 290 | |
| | | | none | Albumin Content | | | | |
| | | 7.0 | 4.25 | pH | | | | |
| | | 1:64 | | Anti-A | | | | |
| | | 1:64 | | Anti-B | | | | |
| | | | | Anti-D | | | | |
| | | 0.5,1,2.5,5 | 6 | Pkg. Sizes | | | | |
| | | 24 | 24 | Shelf Life (mths) | | | | |
| | | Room Temp | Refrigerate | Storage | | | | |
| | | | Refrigerate | | | | | |
| | | 0.01 ml/kg | 4 ml/min | Max Infusion Rate | | | | |

TABLE 1-continued

| IGIV INFORMATION CHART | | | | |
|---|---|---|---|---|
| Belgium | Finland | Hungary | PenPacific | Registration notes |
| | Finland | Hungary | Malysia Pl | Inform. Source |

The invention claimed is:

1. A method for treating an infection by *M. tuberculosis* in a subject in need thereof, comprising identifying a subject in need of treatment for *M. tuberculosis* infection, administering to said subject intravenous immunoglobulin (IVIg), subcutaneous immunoglobulin (SCIg) or intramuscular immunoglobulin (IMIg), wherein said IVIg, SCIg or IMIg comprises an immunoglobulin mixture from at least 1000 individuals; and determining whether said *M. tuberculosis* infection has been treated, wherein a reduction in *M. tuberculosis* titre in said subject by a factor of 10 is indicative of treatment.

2. The method of claim 1, wherein the IVIg, IMIg or SCIg comprises an Immunoglobulin G (IgG) mixture from at least 1000 individuals.

3. The method of claim 1, wherein the IVIg, IMIg or SCIg is at least 90% IgG.

4. The method of claim 1, wherein the IVIg, IMIg or SCIg is human IVIg, IMIg or SCIg.

5. The method of claim 1, wherein the IVIg, IMIg or SCIg is administered intravenously.

6. The method of claim 1, wherein the IVIg, IMIg or SCIg is administered at a dose of 2 g/kg/month.

7. The method of claim 1, wherein the IVIg, IMIg or SCIg is administered in a course of intravenous injections over a period of 2 or more days as a single dose or in repeated doses.

8. The method of claim 1, wherein said IVIg, IMIg or SCIg is administered simultaneously with, prior to, or subsequent to administration of a vaccine.

9. The method of claim 8, wherein said vaccine is the Bacillus Calmette-Guerin vaccine.

10. A method for treating an infection by *M. tuberculosis* in a subject in need thereof, comprising identifying a subject in need of treatment for *M. tuberculosis* infection, administering to said subject intravenous immunoglobulin (IVIg), subcutaneous immunoglobulin (SCIg) or intramuscular immunoglobulin (IMIg), wherein said IVIg, SCIg, or IMIg comprises an immunoglobulin mixture from at least 1000 individuals; and determining whether said *M. tuberculosis* infection has been treated, wherein a reduction in *M. tuberculosis* titre in said subject by a factor of 100 or more is indicative of treatment.

11. The method of claim 10, wherein the IVIg, IMIg or SCIg comprises an Immunoglobulin G (IgG) mixture from at least 1000 individuals.

12. The method of claim 10, wherein the IVIg, IMIg or SCIg is at least 90% IgG.

13. The method of claim 10, wherein the IVIg, IMIg or SCIg is human IVIg, IMIg or SCIg.

14. The method of claim 10, wherein the IVIg, IMIg or SCIg is administered intravenously.

15. The method of claim 10, wherein the IVIg, IMIg or SCIg is administered at a dose of 2 g/kg/month.

16. The method of claim 10, wherein the IVIg, IMIg or SCIg is administered in a course of intravenous injections over a period of 2 or more days as a single dose or in repeated doses.

17. The method of claim 10, wherein said IVIg, IMIg or SCIg is administered simultaneously with, prior to, or subsequent to administration of a vaccine.

18. The method of claim 17, wherein said vaccine is the Bacillus Calmette-Guerin vaccine.

* * * * *